United States Patent

Waskönig et al.

Patent Number: 5,484,423
Date of Patent: * Jan. 16, 1996

[54] NEEDLE, FOR EXAMPLE EPIDURAL NEEDLE

[75] Inventors: Wilhelm Waskönig, Aguadulce; José J. R. Olive, Barcelona, both of Spain

[73] Assignee: te me na Logistics, Spain

[*] Notice: The portion of the term of this patent subsequent to Nov. 15, 2011, has been disclaimed.

[21] Appl. No.: 228,267

[22] Filed: Apr. 15, 1994

Related U.S. Application Data

[63] Continuation-in-part of Ser. No. 50,074, May 5, 1993, Pat. No. 5,364,373.

[30] Foreign Application Priority Data

Apr. 16, 1993 [ES] Spain ...................................... 9300780

[51] Int. Cl.$^6$ .............................. A61M 5/32; A61M 5/31; A61M 5/00

[52] U.S. Cl. ............................................. 604/272; 604/239

[58] Field of Search .................................... 604/117, 264, 604/272–274, 239

[56] References Cited

U.S. PATENT DOCUMENTS

| | | | |
|---|---|---|---|
| 3,540,447 | 11/1970 | Howe | 604/165 |
| 4,002,174 | 1/1977 | Reed et al. | 604/272 |
| 4,335,718 | 6/1982 | Calabrese | 604/272 |
| 4,490,139 | 12/1984 | Huizenga et al. | 604/272 |
| 4,735,612 | 4/1988 | Chevalier | 604/272 |
| 4,781,691 | 11/1988 | Gross | 604/264 |
| 4,861,341 | 8/1989 | Woodburn | 604/272 |
| 4,869,259 | 9/1989 | Elkins | 604/272 |
| 5,364,373 | 11/1994 | Waskonig et al. | 604/272 |

*Primary Examiner*—C. Fred Rosenbaum
*Assistant Examiner*—Frank Wilkens, III

[57] ABSTRACT

The invention refers to a needle (10, 30), such as an epidural needle, whose needle body (14, 28) is structured in its outer surface, at least in sections, so that a resistance which inhibits advance is produced when penetrating through a tissue (22).

6 Claims, 2 Drawing Sheets

NEEDLE, FOR EXAMPLE EPIDURAL NEEDLE

This application is a continuation-in-part of U.S. application Ser. No. 08/050,074, now U.S. Pat. No. 5,364,373 filed May 5,1993 for Epidural Cannula.

BACKGROUND OF THE INVENTION

The invention refers to a needle, such as an epidural needle, in particular intended for lumbar puncture or local anesthesia, comprising a needle point with a preferably lateral opening and ground needle taper as well as a central needle body, preferably possessing a cylindrical shape, the distal end of which can be joined to, for example, a holder, such that in order to position the opening, the needle point penetrates a tissue, in particular during use as an epidural needle, the needle point of which, with its opening, can be positioned between the ligamentum flavum and the dura mater membrane.

A corresponding needle is inferable from, for example, WO 92/07520. To ensure that there is no perforation of the dura mater membrane when the epidural needle is put in place, it is proposed that the needle body possess, at a distance from the needle point, a cross-sectional enlargement such that when a force acts on the epidural needle in the direction of its long axis, its forward movement can be slowed when the enlargement penetrates into the ligamentum flavum. The enlargement can be an expansion or a peripheral bead.

Such epidural needles created, for the first time, the capability of always positioning the needle point with its opening in the epidural space, even under unfavorable conditions, without damaging the dura mater membrane.

The requirement for a cross-sectional enlargement, however, increases the production costs of such epidural needles.

The underlying problem of the present invention is to develop a needle of the aforesaid type, in particular an epidural needle, so as to ensure, with simple design features, that a tissue is penetrated in a controlled fashion and the needle point can be positioned in a space with no danger of undesired tissue damage. In particular, the intent is to allow easy epidural puncture.

According to the invention, the problem is substantially solved by the fact that the needle body is structured in its outer surface, at least in sections, so that a resistance which inhibits advance is produced when penetrating through the tissue.

In particular, provision is made for the outer surface to be structured, for example roughened, in such a way that overcoming the resistance requires 1.7 to 0.3 times the force needed when the needle point penetrates into the tissue.

The outer surface can possess roughening in the range between 0.02 um and 500 um. In particular, the outer surface has a roughness between N3 (0.1 um) and N12 (50 um) according to ISO Standard 1302.

In a preferred embodiment of the invention, however, provision is made for the structuring of the outer surface also to occur in a region that—as in the epidural needle of the aforesaid kind—possesses a cross-sectional enlargement at a distance from the needle point.

These features ensure that an abrupt change in force does not occur when the needle is pushed forward, so that as a result the danger of uncontrolled movements, and therefore of damage to tissues such as the dura mater membrane in particular, is ruled out.

The combination of surface structuring, such as roughening, and cross-sectional enlargement ensures, especially in an epidural needle, that a consistent resistance or steadily changing resistance occurs upon penetration through the ligamentum flavum and into the epidural space, guaranteeing that the needle point cannot perforate the dura mater.

In very general terms, it should be noted that roughness means that as a result of structuring of the surface of the needle, a slowing effect occurs upon penetration of tissue, with the effect described earlier.

Of course the teaching of the invention is not confined to needles that possess only a cylindrical body. Indeed other body geometries, to which the teaching of the invention can be applied, are equally possible. The same applies with reference to the range of applications for the needle.

BRIEF DESCRIPTION OF THE DRAWINGS

Further details, advantages, and features of the invention are evident not only by the Claims and the features inferable therefrom (individually and/or in combination), but also from the description below of an exemplary embodiment inferable from the drawings, in which:

DETAILED DESCRIPTION OF THE PREFERRED EMBODIMENT

Figure 1:
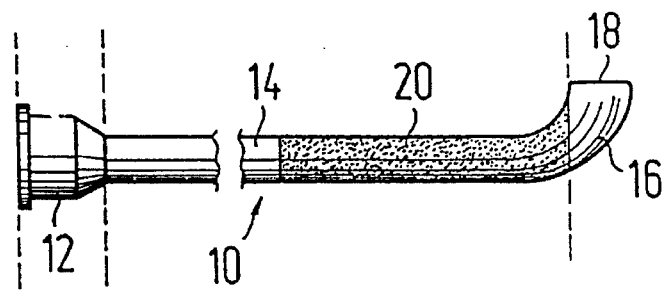
FIG. 1 shows a schematic depiction of a first embodiment of a needle according to the invention.

FIG. 1 depicts, in purely schematic form, a first embodiment of an epidural needle (10) that consists of an enlarged end section (12) that can be slid onto a syringe; a central, preferably hollow cylindrical section (14); and a needle point (16) that possesses an opening (18) extending laterally.

The needle body (14) is roughened locally on the outside. This region is given the reference number (20) in FIG. 1. In the exemplary embodiment, the structured or roughened region (20) begins at the distal region of the opening (18) and ends at a distance from the enlargement (12). The region (20) should possess a length such that during an epidural puncture it lies within the ligamentum flavum (22), whereas the needle point (16) is then located in the epidural space (24) delimited externally [sic] by the dura mater membrane (26).

Figure 3:
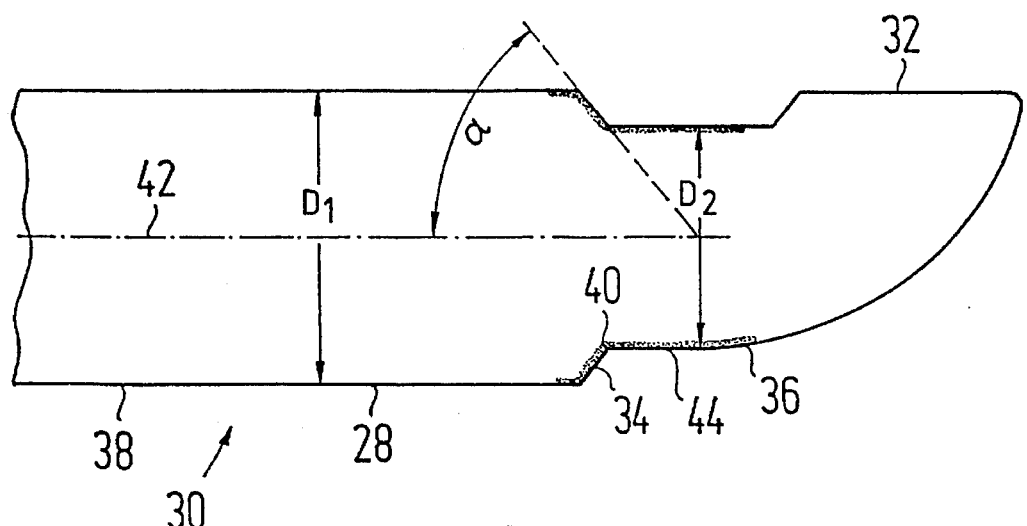
FIG. 3 shows a second embodiment of a needle.

In the exemplary embodiment according to FIG. 3, a needle body (28) of an epidural needle (30) possesses at a distance from its point (32) a cross-sectional enlargement (34) that can correspond to the teaching of WO 92/07520. Consequently the needle body (28) possesses a diameter D2 in the proximal region (36), whereas in the distal region the diameter is D1, which is greater than D2. The transition region (40) between sections (36) and (38) consists of an angle extending at an angle [alpha] to the long axis (42) of the needle, which is preferably between 30 and 60 degrees.

According to the teaching of the invention, the surface of the needle body (28) is structured, such as roughened, at least locally in the proximal region (36) and in the transition region (40) to the distal region (38). This roughened or structured region, which bears the reference number (44), can also extend into the distal region (38), as illustrated by the depiction in the drawing.

Figure 2:
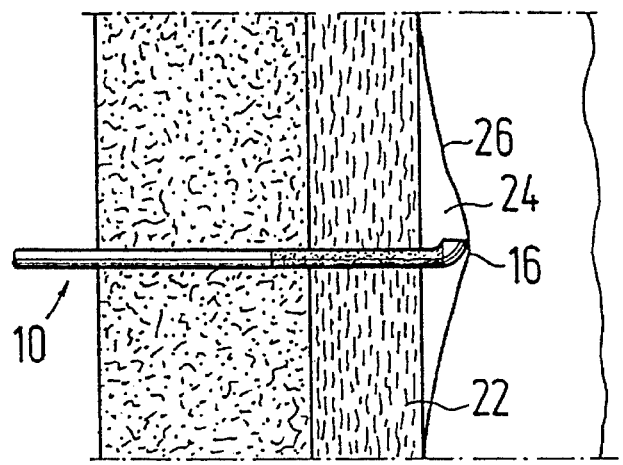
FIG. 2 shows the needle inferable from FIG. 1, with needle opening arranged between the ligamentum flavum and dura mater membrane.
Figure 4:
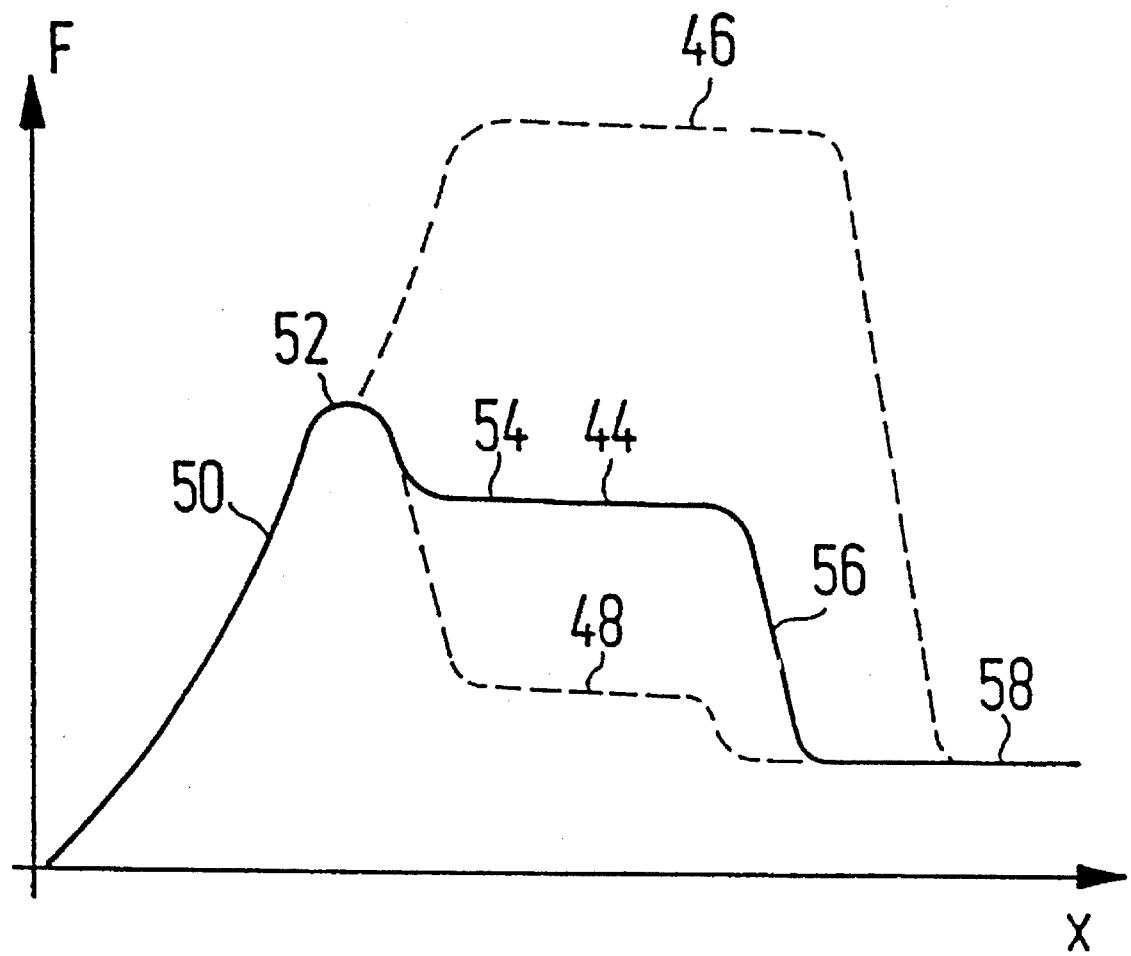
FIG. 4 shows a diagram of distance vs. force, to illustrate the operation of the teaching of the invention.

FIG. 4 is intended to illustrate that because of the roughening of the surface of the needle body (14) or (28) according to the invention, when the ligamentum flavum (22) is penetrated, a change in resistance occurs along the displacement path x as a function of the roughness. The displacement or penetration path is therefore plotted against the applied force F required to push the needle (10) according to FIG. 2 through the ligamentum flavum (22) and position the needle point (16) with its opening (18) in the epidural space (24).

The curves (44), (46), and (48) represent epidural needles according to the invention with different surface roughnesses or lengths thereof.

The solid rising segment (50) of curve (44) coincides with the corresponding resistance profile of curves (46), (48), i.e. is independent of roughness. Once the needle point (16) enters the ligamentum flavum (22) (bump (52) in curve (44)), a change in resistance occurs, such that upon further penetration of the ligamentum flavum the resistance decreases if the surface possesses an average roughness of 0.1 um (curve (44)).

As long as the roughened region (20) is located within the ligamentum flavum (22), the force to be applied during penetration remains constant (plateau (54)). As soon as the roughened region leaves the ligamentum flavum (22), a sudden change in resistance (section (56)) occurs, and merges into a constant value (58).

Curve (46) is characteristic of a roughening that is coarser as compared to curve (44) and is approximately 200 um, and possesses a greater length along the long axis of the needle body (14).

Curve (48), on the other hand, represents a roughening of a needle body with a low roughness of 0.02 um, which also extends over a shorter length in comparison with the needles represented by curves (44) and (46).

Regardless of the degree of roughness, curves (44), (46), and (48) furthermore illustrate that the resistance evoked by the roughness upon penetration of the ligamentum flavum (22) is always greater than that of an epidural needle with a smooth surface (region (58) of the curves).

We claim:

1. A needle usable as an epidural needle for lumbar puncture or local anesthesia, including a needle point with a lateral opening therein, a central needle body, and a distal end which is connectable to a holder, the needle point, in use, penetrating tissue and positioning its opening between the ligamentum flavum and the dura mater membrane;

the invention comprising said needle body having an outer surface, said outer surface of the needle body having a roughness between N3 (0.1 μm) and N2 (50 μm) according to ISO standard 1302 thereon, for providing a resistance which inhibits advance when penetrating through tissue, said needle body having a cross-sectional enlargement at a distance from the needle point, the outer surface of the needle body having the roughness locally in the region of the cross-sectional enlargement.

2. Needle according to claim 1, wherein the outer surface of the needle body also has roughness forwardly from the cross-sectional enlargement toward the point.

3. Needle according to claim 2, wherein the outer surface roughness is such that penetration through the tissue requires 1.7 to 0.3 times the force needed without roughness when the needle point penetrates into tissue.

4. A needle usable as an epidural needle for lumbar puncture or local anesthesia, including a needle point with a lateral opening therein, a central needle body, and a distal end which is connectable to a holder, the needle point, in use, penetrating tissue and positioning its opening between the ligamentum flavum and the dura mater membrane;

the invention comprising said needle body having an outer surface, said outer surface of the needle body having roughening in the range between 0.02 μm and 500 μm thereon, for providing a resistance which inhibits advance when penetrating through tissue, said needle body having a cross-sectional enlargement at a distance from the needle point, the outer surface of the needle body having the roughening locally in the region of the cross-sectional enlargement.

5. Needle according to claim 4, wherein the outer surface of the needle body also has roughening forwardly from the cross-sectional enlargement toward the point.

6. Needle according to claim 5, wherein the outer surface roughening is such that penetration through the tissue requires 1.7 to 0.3 times the force needed without roughening when the needle point penetrates into tissue.

* * * * *